US012678470B2

(12) United States Patent
Chatman

(10) Patent No.: US 12,678,470 B2
(45) Date of Patent: Jul. 14, 2026

(54) MULTI-PURPOSE MEDICINAL CREAM

(71) Applicant: Angela Chatman, Maricopa, AZ (US)

(72) Inventor: Angela Chatman, Maricopa, AZ (US)

( * ) Notice: Subject to any disclaimer, the term of this patent is extended or adjusted under 35 U.S.C. 154(b) by 219 days.

(21) Appl. No.: 18/798,395

(22) Filed: Aug. 8, 2024

(65) Prior Publication Data

US 2026/0041727 A1 Feb. 12, 2026

(51) Int. Cl.
A61K 36/00 (2006.01)
A61K 36/28 (2006.01)

(52) U.S. Cl.
CPC .................................. A61K 36/28 (2013.01)

(58) Field of Classification Search
None
See application file for complete search history.

(56) References Cited

U.S. PATENT DOCUMENTS

| | | |
|---|---|---|
| 8,821,921 B2 | 9/2014 | Lyftogt |
| 2018/0369174 A1 | 12/2018 | Frangakis et al. |
| 2020/0345686 A1 | 11/2020 | Baillo et al. |

FOREIGN PATENT DOCUMENTS

| | | |
|---|---|---|
| EP | 3270906 B1 | 9/2016 |
| WO | 2013062424 A1 | 5/2013 |

OTHER PUBLICATIONS https://www.webmd.com/drugs/2/drug-149434/hydrocortisone-aloe-vitamins-a-d-and-e-topical/details#:~:text=This%20medication%20is%20used%20to,female%20genitals%2C%20anal%20itching.
https://www.avacaremedical.com/skin-wound-care/skin-protection-and-cleansers/barrier-cream/vitamin-a-and-d-ointment.
https://www.cvs.com/shop/a-d-first-aid-ointment-with-vitamin-a-and-d-prodid-1011833?skuId=409818&cgaa=QWxsb3dHb29nbGVUb0FjY2Vzc0NWU1BhZ2Vz&cid=ps_summer_fa_pla_test&gclid=CjwKCAjw69moBhBgEiwAUFCx2N16ZYtevxk0pE78ao6LPBv5h7UJqnjocbjHWQoHZk7B7-8ZyFDUSBoC9m4QAvD_BwE&gclsrc=aw.ds.
https://www.amazon.com/Vitamin-Moisterizing-Soothing-Cream-Bottles/dp/B089FQ6877?source=ps-sl-shoppingads-lpcontext&ref_=fplfs&psc=1&smid=A1CCMYZ90QAIFA.

*Primary Examiner* — Russell G Fiebig
(74) *Attorney, Agent, or Firm* — Peter Borsari

(57) ABSTRACT

A multi-purpose medicinal cream comprising shea butter, wild opium lettus powder, Orange Blood, Frankincense, Lavender, Rosemary, Copaiba Balsam, Birch Sweet, Lemon Grass, Marjoram, Basil, Eucalyptus, Peppermint, Cinnamon, Cedarwood, Thyme, Clove, Vetiver, Geranium, Cinnamon Leaf, and Ylang Ylang. The multi-purpose cream is an aid in pain management of disorders including lupus, arthritis, rheumatoid arthritis, knee and joint pain, neck pain, inflammation, migraines, and neuropathic disorders, as well the treatment of skin conditions including eczema, dry skin, psoriasis, swelling, heat rash, rashes, and rashes of dogs.

9 Claims, No Drawings

MULTI-PURPOSE MEDICINAL CREAM

BACKGROUND OF THE INVENTION

Essential oils have been used for centuries for numerous medicinal purposes, either alone, or in combination as a blend of oils. Many essential oils have anti-inflammatory properties, anti-arthritic properties, and pain-relieving properties. Other essential oils have been used to treat a variety of skin conditions, including, for example, acne, eczema, rashes, and psoriasis. And some essential oils also act as natural skin energizers, astringents, and moisturizers. Essential oils are too strong to use in their pure form. Typically, they are diluted with other oils, creams, or gels to attain a solution that contains a small percentage of the essential oil.

PRIOR ART

The prior art is replete with creams and lotions that provide creams containing one or more essential oils for to treat pain, inflammation, or to enhance the skin. For example, U.S. Pat. No. 8,821,921 B2 to Lyftogt discloses the use of Vitamin D in a medicament for treatment of neurogenic inflammation. U.S. Patent Application Publication 2018/0369174 A1 to Frangakis et al and U.S. Patent Application Publication 2020/0345686 A1 to Baillo et al. disclose therapeutic compositions for treating neuropathic pain or skin conditions. WO 2013/062424 A1 to Cushman et al. relates to another formation comprising Vitamin D for the treatment of pain and/or inflammation. And, EP Patent 3,270,906 B1 also provides a composition for the treatment of neuropathic pain. While these prior art references disclose the use of one or more natural oils or vitamins in the formulation, they do not contemplate a medicinal cream which can aid pain relief management and which is capable of treating multiple skin conditions. Accordingly, a need still exists for a multi-purpose medicinal cream containing all natural ingredients which can be used to aid or treat pain-related disorders such as lupus, arthritis, rheumatoid arthritis, knee and joint pain, neck pain, heel pain, hamstring pain, neuropathic disorders, miscellaneous aches, and migraines as well as treat skin conditions including burns, dry skin, eczema, psoriasis, inflammation, rashes, heat rash, scars, cuts, as well as rashes on dogs.

SUMMARY OF THE INVENTION

The invention of the present subject matter relates to a multi-purpose medicinal cream comprising shea butter, wild opium lettus powder and the following essential oils: Orange Blood, Frankincense, Lavender, Rosemary, Copaiba Balsam, Birch Sweet, Lemon Grass, Marjoram, Basil, Eucalyptus, Peppermint, Cinnamon, Cedarwood, Thyme, Clove, Vetiver, Geranium, Cinnamon Leaf, and Ylang Ylang to treat pain from numerous disorders and treat skin conditions.

Accordingly, it is an object of the present subject matter to provide multi-purpose medicinal cream comprising shea butter, wild opium lettus powder and a mixture of essential oils to aid in the treatment of pain management for disorders including as lupus, arthritis, rheumatoid arthritis, knee and joint pain, neck pain, heel pain, hamstring pain, neuropathic disorders, miscellaneous aches, and migraines.

It is another object of the present subject matter to provide shea butter, wild opium lettus powder and a mixture of essential oils to aid in the treatment of skin conditions including burns, dry skin, eczema, psoriasis, inflammation, rashes, heat rash, scars, cuts, as well as rashes on dogs.

It is still another object of the present subject matter to provide a multi-purpose medicinal cream comprising shea butter, wild opium lettus powder, Orange Blood, Frankincense, Lavender, Rosemary, Copaiba Balsam, Birch Sweet, Lemon Grass, Marjoram, Basil, Eucalyptus, Peppermint, Cinnamon, Cedarwood, Thyme, Clove, Vetiver, Geranium, Cinnamon Leaf, and Ylang Ylang.

These and other objects of the present subject matter are accomplished by providing a multi-purpose medicinal cream comprises from about 3.5 cups (28 fluid ounces) to about 4.5 cups (36 fluid ounces) of shea butter, from about 1000 mg to about 1400 mg of wild opium lettus powder, and from about 35 drops (0.0592 fluid ounces) to about 45 drops (0.076) fluid ounces) of each of the following essential oils: Orange Blood, Frankincense, Lavender, Rosemary, Copaiba Balsam, Birch Sweet, Lemon Grass, Marjoram, Basil, Eucalyptus, Peppermint, Cinnamon, Cedarwood, Thyme, Clove, Vetiver, Geranium, Cinnamon Leaf, and Ylang Ylang

DETAILED DESCRIPTION OF THE INVENTION

In the following description, numerous specific details are set forth to clearly describe various specific embodiments disclosed herein. One skilled in the art, however, will understand that the presently claimed invention may be practiced without all the specific details discussed below. In other instances, well know features have not been described so as to not obscure the invention.

It is to be understood that the phraseology and terminology used herein is for the purpose of description and should not be regarded as limiting. The use of the terms "including", "comprising", "having", and variations thereof herein is meant to encompass the items listed thereafter and equivalents thereof as well as additional items.

The present subject matter is directed multi-purpose medicinal cream comprising shea butter, wild opium lettus powder and a mixture of essential oils. The medicinal cream composition and particularly the inventive mixture of essential oils, is the result of extensive research and experimentation to maximize the effects of this unique combination of natural ingredients to promote pain relief, including pain relief from migraines, knee and joint pain relief, arthritis and the like, and skin treatments, such as eczema, psoriasis, rashes, heat rash and rashes on dogs.

The medicinal cream of the present subject matter uses Shea butter as the carrier. Shea butter is a fat extracted from the nut of the African shea tree. It is widely used in cosmetics as a moisturizer, salve, or lotion. Shea butter acts as an emollient and contains substances that can reduce skin swelling and can aid in the treatment of certain ailments associated with skin swelling, such as eczema. Wild opium lettus (lettuce) has been used in traditional medicine for pain relief for centuries. Some studies suggest the plant has analgesic and sedative properties as well as potential pain-relieving, anti-arthritic, and anti-inflammatory properties.

The mixture of the selected essential oils utilized in the multi-purpose medicinal cream of the present subject matter is considered unique in aiding a variety of ailments. Each of the essential oils has some therapeutic value and some of these essential oils have been used in combination. However, the mixture of the essential oils described below yields a multi-purpose medicinal cream that can treat a diverse array of disorders.

Apart from its detoxifying properties, Orange Blood acts as a natural skin energizer as the oil is capable of penetrating deeply into the skin's pores, detoxifying the skin and enhancing the formation of collagen, which then results in skin that is soft, smooth, and plump.

Frankincense, also known as olibanum, is made from the resin of the Boswellia tree. This tree typically grows in the dry, mountainous regions of India, Africa, and the Middle East. Frankincense can prevent the release of leukotrienes and compounds that cause inflammation.

Lavender is an herb native to the Mediterranean region and is one of most widely grown essential oil crops in the world. Typically used in aromatherapy and skin lotion formulations, Lavender oil has many significant properties including skin-healing can promote wound healing. It speeds up the rate of healing, increases the expression of which keeps your skin elastic and your joints healthy—and enhances the activity of proteins involved in rebuilding tissue.

Rosemary essential oil is widely known for its high antioxidant, anti-inflammatory, and neurological properties, the anti-inflammatory properties may help reduce tissue which typically can lead to joint pain, swelling, and stiffness. Rosemary oil also has been studied to help provide pain relief in rheumatic diseases like fibromyalgia, rheumatoid arthritis, and osteoarthritis.

Copaiba Balsam is an oleoresin which has been used in traditional medicine for its anti-inflammatory, analgesic, and antiseptic properties. It also has been utilized to treat a variety of skin conditions, including acne, eczema, and psoriasis. Birch Sweet oil is rich in methyl salicylates and salicylic acid that help promote the body's ability to boost its healing cycles. Traditionally, birch oil has been used as an astringent for its effectiveness in toning and tightening of the skin. Birch Oil also is known for soothing minor pain and topical inflammation.

The essential oil from Lemongrass contains citral which may help ease pain as it relieves inflammation. Lemongrass oil also has antibacterial properties, antifungal properties, anti-inflammatory properties, and antioxidant properties. Topical application of this essential oil has been shown to relieve pain associated with arthritis.

Marjoram oil is well-known for its ability to balance hormones and, as a result, improve skin health. Basil oil also is known to balance the skin's natural oil levels, including calming irritation and itchiness, as well as soothing minor cuts and scrapes. Eucalyptus is regarded highly for its ability in aiding the treatment and prevention of acne. It also has anti-inflammatory properties which reduce redness and other inflammatory skins conditions. Peppermint oil peppermint has proven to have some antioxidant properties, mild antibacterial properties, and anti-inflammatory properties.

Different parts of the cinnamon tree give two different oils: cinnamon bark essential oil (i.e. cinnamon oil) and cinnamon leaf essential oil, with cinnamon bark oil being the more potent. Both essential oils have antimicrobial and anti-inflammatory properties and enhance circulation and nourish the skin. Cinnamon oil has been used to treat dry skin, acne, and rashes, as well as alleviate aches, pains, and stiffness associated with the muscles and joints.

Cedarwood oil has anti-inflammatory and antimicrobial properties and has been used for treating acne, particularly alleviating and reducing stubborn breakouts. Cedarwood oil also be beneficial for other skin conditions, for example, reducing the appearance of scars, treating minor wounds, as well as soothing and alleviating pain.

Thyme Oil also is known for improving skin health, promoting circulation, and increasing blood flow to the skin.

As a result of Thyme oil's remarkable ability to increase circulation, scar tissue from acne or other skin injuries are known to slowly fade.

Clove oil been an integral part of traditional and folk medicines and is known as a powerful anti-aging ingredient, removing dead skin cells, and aiding in blood circulation, having anti-parasitic, antiviral, antioxidant, and antimicrobial properties. When clove oil is applied topically, users can benefit from its anti-inflammatory, antifungal and antibacterial properties, which can help to prevent or aid in the treatment of a variety of skin conditions and fungal infections. A 2017 study found that clove oil can help to reduce chronic itching, with participants revealing they saw a significant drop in skin irritation and the sensation that causes them to scratch.

Vetiver oil is yet another remarkable essential oil used in skin cell regeneration and boosting the growth of new cells, aiding in wound healing, effectively reduces scars, blemishes, and marks due to acne, burns or pox by removing dead skin cells from the body. Vetiver oil also is known for its anti-inflammatory properties.

Geranium is an essential oil having anti-inflammatory properties and is proven to be beneficial in aiding in the treatment of numerous inflammatory conditions effecting the skin. Ylang Yang is derived from the flowers of Cananga odorata genuina. This essential oil has been topically applied to the skin to balance and regulate oil production. It soothes inflammation and irritation on the skin and is loaded with properties that helps to heal minor wounds, prevent microbial growth, and protects against viral, fungal, and bacterial infections.

In a preferred embodiment of the present subject matter, the multi-purpose medicinal cream comprises from about 3.5 cups (28 fluid ounces) to about 4.5 cups (36 fluid ounces) of shea butter, from about 1000 mg to about 1400 mg of wild opium lettus powder, and from about 35 drops (0.0592 fluid ounces) to about 45 drops (0.076) fluid ounces) of each of the following essential oils: Orange Blood, Frankincense, Lavender, Rosemary, Copaiba Balsam, Birch Sweet, Lemon Grass, Marjoram, Basil, Eucalyptus, Peppermint, Cinnamon, Cedarwood, Thyme, Clove, Vetiver, Geranium, Cinnamon Leaf, and Ylang Ylang. More preferably, the multi-purpose medicinal cream comprises about 4.0 cups (32 fluid ounces) of shea butter, about 1200 mg of wild opium lettus powder, and about 40 drops (0.0676 fluid ounces) of each of the following essential oils: Orange Blood, Frankincense, Lavender, Rosemary, Copaiba Balsam, Birch Sweet, Lemon Grass, Marjoram, Basil, Eucalyptus, Peppermint, Cinnamon, Cedarwood, Thyme, Clove, Vetiver, Geranium, Cinnamon Leaf, and Ylang.

The multi-purpose medicinal cream of the present subject matter has proven results in aiding pain management of numerous disorders including lupus, arthritis, rheumatoid arthritis, knee and joint pain, neck pain, inflammation, migraines, and neuropathic disorders. The multi-purpose medicinal also has been used successfully in the treatment of eczema, dry skin, psoriasis, swelling, heat rash, rashes, and rashes of dogs.

While several illustrative embodiments of the invention have been shown and described, numerous variations and alternative embodiments will occur to those skilled in the art. Such variations and alternative embodiments are contemplated and can be made without departing from the scope of the invention as defined in the appended claims.

The invention claimed is:

1. A multi-purpose medicinal cream comprising:
  a. from about 3.5 cups (28 fluid ounces) to about 4.5 cups (36 fluid ounces) of shea butter;
  b. from about 1000 mg to about 1400 mg of wild opium lettus, and
  c. a blend comprising about 35 drops (0.0592 fluid ounces) to about 45 drops (0.076 fluid ounces) of each of the following essential oils:
    i. orange blood;
    ii. frankincense;
    iii. lavender;
    iv. rosemary;
    v. copaia balsam;
    vi. birch sweet;
    vii. lemongrass;
    viii. marjoram;
    ix. basil;
    x. eucalyptus;
    xi. peppermint;
    xii. cinnamon;
    xiii. cedarwood;
    xiv. thyme;
    xv. clove;
    xvi. vetiver;
    xvii. geranium;
    xviii. cinnamon leaf, and
    xix. ylang ylang.

2. The multi-purpose medicinal cream in accordance with claim 1 for use in aiding pain management of disorders including lupus, arthritis, rheumatoid arthritis, knee and joint pain, neck pain, inflammation, migraines, and neuropathic disorders.

3. The multi-purpose medicinal cream in accordance with claim 1 for use in the treatment of skin conditions, eczema, dry skin, psoriasis, swelling, heat rash, rashes, and rashes of dogs.

4. A multi-purpose medicinal cream consisting essentially of:
  a. about 4 cups (32 fluid ounces) of shea butter;
  b. about 1200 mg of wild opium lettus, and
  c. a blend comprising about 40 drops (0.0676 fluid ounces) of each of the following essential oils:
    i. orange blood;
    ii. frankincense;
    iii. lavender;
    iv. rosemary;
    v. copaia balsam;
    vi. birch sweet;
    vii. lemongrass;
    viii. marjoram;
    ix. basil;
    x. eucalyptus;

xi. peppermint;
    xii. cinnamon;
    xiii. cedarwood;
    xiv. thyme;
    xv. clove;
    xvi. vetiver;
    xvii. geranium;
    xviii. cinnamon leaf, and
    xix. ylang ylang.

5. The multi-purpose medicinal cream in accordance with claim 4 for use in aiding pain management of disorders including lupus, arthritis, rheumatoid arthritis, knee and joint pain, neck pain, inflammation, migraines, and neuropathic disorders.

6. The multi-purpose medicinal cream in accordance with claim 4 for use in the treatment of skin conditions, eczema, dry skin, psoriasis, swelling, heat rash, rashes, and rashes of dogs.

7. A multi-purpose medicinal cream consisting of:
  a. about 4 cups (32 fluid ounces) of shea butter;
  b. about 1200 mg of wild opium lettus, and
  c. a blend comprising about 40 drops (0.0676 fluid ounces) of each of the following essential oils:
    i. orange blood;
    ii. frankincense;
    iii. lavender;
    iv. rosemary;
    v. copaia balsam;
    vi. birch sweet;
    vii. lemongrass;
    viii. marjoram;
    ix. basil;
    x. eucalyptus;
    xi. peppermint;
    xii. cinnamon;
    xiii. cedarwood;
    xiv. thyme;
    xv. clove;
    xvi. vetiver;
    xvii. geranium;
    xviii. cinnamon leaf, and
    xix. ylang ylang.

8. The multi-purpose medicinal cream in accordance with claim 7 for use in aiding pain management of disorders including lupus, arthritis, rheumatoid arthritis, knee and joint pain, neck pain, inflammation, migraines, and neuropathic disorders.

9. The multi-purpose medicinal cream in accordance with claim 7 for use in the treatment of skin conditions including eczema, dry skin, psoriasis, swelling, heat rash, rashes, and rashes of dogs.

* * * * *